United States Patent
Cise et al.

(10) Patent No.: US 6,615,835 B1
(45) Date of Patent: Sep. 9, 2003

(54) FLEXIBLE MULTIPLE PORT ADAPTOR

(75) Inventors: David M. Cise, Herriman, UT (US); V. Roland Smith, Salt Lake City, UT (US); Rick D. Lorenzen, Battle Creek, IA (US)

(73) Assignee: Ballard Medical Products, Draper, UT (US)

( * ) Notice: Subject to any disclaimer, the term of this patent is extended or adjusted under 35 U.S.C. 154(b) by 0 days.

(21) Appl. No.: 09/398,704

(22) Filed: Sep. 20, 1999

(51) Int. Cl.[7] .......................... A61M 16/00; A62B 9/06
(52) U.S. Cl. ........................ 128/207.14; 128/200.26; 128/207.15; 128/207.16
(58) Field of Search .................. 128/200.26, 207.14, 128/207.15, 207.16; 604/539, 533, 534, 538, 204

(56) References Cited

U.S. PATENT DOCUMENTS

| | | | |
|---|---|---|---|
| 3,991,762 A | | 11/1976 | Radford |
| 4,198,983 A | * | 4/1980 | Becker et al. .............. 128/349 |
| 4,351,328 A | | 9/1982 | Bodai |
| 4,723,543 A | * | 2/1988 | Beran ..................... 128/207.14 |
| 5,101,817 A | * | 4/1992 | Etter ...................... 128/200.26 |
| 5,250,040 A | * | 10/1993 | Parks et al. .................. 604/283 |
| 5,309,906 A | * | 5/1994 | LaBombard ........... 128/207.14 |
| 5,329,921 A | * | 7/1994 | Socaris et al. .......... 128/207.14 |
| 5,354,267 A | | 10/1994 | Niermann et al. |
| 5,368,017 A | * | 11/1994 | Sorenson et al. ...... 128/200.26 |
| 5,403,291 A | * | 4/1995 | Abrahamson ............... 604/280 |
| 5,431,157 A | | 7/1995 | Mourkidou et al. |
| 5,492,109 A | * | 2/1996 | Hirschl et al. ......... 128/201.21 |
| 5,735,271 A | | 4/1998 | Lorenzen et al. |
| 5,738,091 A | * | 4/1998 | Kee et al. .............. 128/205.12 |
| 5,775,325 A | * | 7/1998 | Russo .................... 128/205.12 |
| 5,824,173 A | * | 10/1998 | Fontirroche et al. .......... 156/86 |
| 5,952,423 A | * | 9/1999 | Shang et al. .................. 525/64 |
| 6,086,529 A | * | 7/2000 | Arndt .......................... 600/114 |
| 6,237,597 B1 | * | 5/2001 | Kovac ................... 128/207.14 |
| 6,261,273 B1 | * | 7/2001 | Ruiz .......................... 604/284 |

FOREIGN PATENT DOCUMENTS

| | | |
|---|---|---|
| DE | 2920366 A1 | 11/1980 |
| DE | 2939794 A1 | 4/1981 |

OTHER PUBLICATIONS

International Search Report, Feb. 1, 2001.
Verified Translation of DE 29 20 366 A1, Nov. 19, 2001.
Verified Translation of DE 29 39 794 A1, Nov, 19, 2001.

* cited by examiner

*Primary Examiner*—Weilun Lo
*Assistant Examiner*—Darwin P. Erezo
(74) *Attorney, Agent, or Firm*—Dority & Manning, P.A.

(57) ABSTRACT

A flexible multiple port adaptor has an adaptor body which includes a distal portion defining a distal channel and a proximal portion defining a first proximal channel and a second proximal channel. As least one of the first and second proximal channels is normally disposed out of alignment with the distal channel. However, because the adaptor body is flexible, the adaptor body may be manipulated so that channel(s) which are out of alignment with the distal channel may be placed into alignment with the distal channel so that a medical instrument can be advanced through the channels without bending the medical instrument.

45 Claims, 6 Drawing Sheets

FLEXIBLE MULTIPLE PORT ADAPTOR

BACKGROUND OF THE INVENTION

1. Field of the Invention

The present inventions relate to adaptors for use with intubated patients, and more particularly to novel multiple port access adaptors which may be used with a variety of different medical treatment devices simultaneously. Such treatment devices may include those designed for ventilation, aspiration, monitoring, visualizing, imaging, sampling and therapeutic delivery devices which are used on intubated patients.

2. State of the Art

There are a variety of different circumstances under which a person may be intubated. In intubation, an artificial airway, such as an endotracheal tube, is placed in the upper respiratory system of a patient to facilitate respiration. In some circumstances, such as surgery, the artificial airway is temporary and is used for anesthesia and proper ventilation and oxygenation. In many other situations, however, the endotracheal tube will be left in the patient for a prolonged period of time. With many traumatic accident victims, for example, the artificial airway will remain in place to sustain mechanical ventilation for the life of the patient.

Respiratory patient care has changed dramatically over the past three decades. Advances in medical technology have greatly increased the number of medical devices which are available for addressing problems associated with respiratory care. For example, if an endotracheal tube is to be left in place for more than a brief period of time, it is critical that respiratory secretions be periodically removed. This is most often accomplished with the use of a respiratory suction catheter which is advanced into the endotracheal tube. As the suction catheter is withdrawn, a negative pressure is applied to the interior of the catheter to draw mucus and other obstructions from the patient's respiratory system.

Advanced medical devices which are available for use in respiratory care are not limited to endotracheal suction catheters. Improvements have been made in devices, such as bronchoscopes, which are used for visualizing the patient's respiratory system. Other advances have facilitated the introduction of catheters to provide medical fluids to and from the lungs. Yet other advances have facilitated the sampling of respiratory tissues and secretions, therapeutic delivery of medication and other procedures.

The availability of these advanced medical devices has greatly improved the quality of life for those who must be intubated. Procedures today are generally less discomforting to the patient and are more efficacious. A dilemma is presented, however, in providing access to each of a number of medical devices to the patient at the same time. Traditionally, if a certain respiratory treatment device was needed, the patient was removed from other devices until the procedure was completed.

An extreme example of this practice is present in the use of open suction catheters. Until the 1980s, each time the patient's respiratory system needed to be suctioned, it was common to disconnect the patient's artificial airway from the manifold and ventilator tubes which supplied the patient with air. Interference with the air supply to the patient, even if only for a few seconds, was often severely distressing to the patient. These problems were initially overcome in the invention disclosed in U.S. Pat. No. 3,991,762 to Radford.

Radford developed what is commonly referred to as a closed suction catheter system. In a closed suction catheter system, a catheter is maintained within a protective sleeve which is attached to a manifold which also receives the tubing of the ventilator which delivers air to the patient's lungs. When suctioning is desired, the catheter is advanced through the manifold and into the artificial airway. Negative pressure is then applied to the catheter and secretions within the patient's respiratory system are evacuated.

The Radford system and its successors are advantageous in that they allow the patient's ventilation to continue throughout the suctioning procedure. Additionally, they do not require the closed circuit to be broken (i.e. opened to outside air) for each suctioning procedure.

It is highly desirable to have these closed suction catheter systems attached to the endotracheal tube or other artificial airway of the patient. Doing so in the conventional manner, however, requires the closed suction catheter system to be disconnected from the patient to allow use of other devices such as bronchoscopes, oxygen supplementation catheters, tissue sampling devices, and the like. The endotracheal catheter system must then be reattached once the other device is no longer needed.

Breaking the circuit in this manner increases the risk of nosoccomial infections and increases the risk that clinicians will come into contact with mucus and other secretions of the patient. Additionally, it consumes time which the clinician could use to treat other patients.

In order to alleviate the safety and productivity issues, numerous attempts have been made to develop multiple port adaptors for use with endotracheal tubes. While not an exhaustive analysis of the configurations which have been set forth in the art, FIGS. 1A and 1B show typical attempts to provide a multi-port adaptor for use with endotracheal tubes and are discussed in detail below.

The adaptors of the prior art fall into two general categories—fixed and rotatable. In the fixed category, as shown in FIGS. 1A, the adaptor, generally indicated at 10, is typically made from a single piece of rigid material, such as acrylic or polypropylene. The adaptor 10 forms a generally T-shaped, elbow-like housing 14 with a first barrel 18 having an open distal end 18a forming a first, distal port to the housing 14. The interior surface 22 of the first barrel 18 forms a distal channel for receiving the proximal end of an endotracheal tube (not shown).

A fourth barrel 60 providing a fourth port 66 extends from the housing 14 on a side of the housing opposite the second barrel 26. The fourth port 66 allows for a second catheter assembly 70 to be used with the housing 14. As shown in FIG. 1A, the catheter assembly is configured to provide medical fluids directly into and from the patient's lungs. To this end, a catheter 74 of the catheter assembly 70 is connected to an oxygen source 20.

A third port 34 is formed by a third barrel 38 which is disposed along a common axis with the first barrel 18. The orientation of the third barrel 38 facilitates the advancement of a catheter 42 of an endotracheal suction catheter assembly, generally indicated at 46, through the third and first barrels 34 and 18, respectively. The catheter 42 may thus be advanced down the endotracheal tube and used to suction mucus and other secretions from the patient's respiratory system.

If desired, a lavage port 50 can be provided on the third barrel 38 to facilitate cleaning of the catheter 42. Most such catheter assemblies, however, include a lavage port for cleaning.

A fourth barrel 60 providing a fourth port 64 extends from the housing 14 on a side of the housing opposite the second barrel 26. The fourth port 64 allows for a second catheter assembly 70 to be used with the housing 14. As shown in FIG. 1A, the catheter assembly is configured to provide medical fluids directly into and from the patient's lungs. To this end, a catheter 74 of the catheter assembly 70 is connected to an oxygen source 78.

The configuration of shown in FIG. 1A is a significant improvement over the prior configurations which required the endotracheal suction catheter assembly 46 to be removed prior to use of another device. The housing 14, however, has a disadvantage. In order to operate both the first and second catheter assemblies, or other devices, at least one of the assemblies must be brought or taken out of alignment with the long axis of the housing (i.e. the axis along which the first and third barrels 18 and 38 are disposed). Thus, at least one of the instruments advanced through the manifold must bend to enter the endotracheal tube. For many instruments, such as bronchoscopes, forced bending is undesirable because it increases mechanical wear and distortion. Additionally, instruments commonly have mucus or other secretions on them as they are withdrawn. Instead of carrying the secretion to the proximal ends of the housing (i.e. the third or fourth ports) where the mucus may be easily removed, the mucus may be scraped off in the first barrel 18. The mucus may reenter the patient through the endotracheal tube, may work its way down the ventilation circuit, or may remain in the adaptor 14 and serve as a medium for microbial growth.

FIG. 1B shows yet another attempt to solve the problems associated with obtaining access to the endotracheal tube for multiple instruments. An adaptor housing, generally indicated at 114, is provided with a distal, first barrel 118 having a port formed at the distal end 118a and a distal channel 122 for receiving the proximal end of an endotracheal tube. A second barrel 126 extends laterally from the first barrel 118 and forms a second port 130. A swivel structure 132 may be placed in the port 130 to provide a rotatable attachment between the housing 114 and the wye adaptor of a ventilation circuit (not shown).

As with the embodiment in FIG. 1A, a third barrel 138 extends along a common axis with the first barrel 118. The third barrel 138 includes an opening 134, but the opening does not form a port in that it is not exposed. Rather, a circular flange 140 is disposed about the opening 134. A circular cap 144 is configured to engage and rotate about the circular flange 140. A fourth barrel 148 and a fifth barrel 152 are disposed on the cap 144 so that rotation of the cap alternatively aligns the fourth barrel 148 and the fifth barrel 152 with the opening 134 in the third barrel 138. Thus, the fourth barrel 148 forms a third port 156, and the fifth barrel 152 forms a fourth port 164. Seals 168 may be provided to maintain a substantially airtight seal between the fourth and fifth barrels 148 and 152 and the remainder of the housing 114. A lavage port 162 may also be provided.

In use, a permanent instrument, such as a closed endotracheal suction catheter 168 is usually attached to one port, while the other port is provided with a cap 172 so that the port can be used with a temporary instrument, such as a bronchoscope, without leaving the interior of the housing open. Failing to cover or close the ports subjects both the clinician and the patient to increased risks of cross-contamination.

The configuration shown in FIG. 1B is advantageous in that it allows the port in use to be in axial alignment with the channels extending through the first and third barrels 118 and 138 and axial with the endotracheal tube opening. Thus, a catheter or other instrument is not required to bend as it is passed through the housing 114. Unfortunately, the embodiment shown in FIG. 1B is relatively expensive to make, in that it has several parts which must be molded and then assembled. Additionally, it can be somewhat cumbersome to use, and the ports can be inadvertently rotated, thereby causing misalignment.

Thus, there is a need for a multiple port adaptor which enables a catheter or other instruments to be advanced in a substantially straight line regardless of which port is being used. There is also a need for such a device which is inexpensive and easy to use.

OBJECTS AND SUMMARY OF THE INVENTION

It is an object of the present invention to provide an improved multiple port adaptor which is easy to use and relatively inexpensive.

It is another object of the invention to provide a multiple port adaptor which does not force catheters or other instruments to be bent as they are passed through the adaptor.

It is yet another aspect of the present invention to provide a multiple port adaptor in which the various ports can be used simultaneously, if necessary.

It is still yet another aspect of the present invention to provide a multiple port adaptor which is formed from a single piece of material.

The above and other objects of the invention are realized in specific illustrated embodiments of a multiple port adaptor including an adaptor body having distal end with a distal port, and at least two proximal portions in communication with the distal end, each of the proximal portions forming a proximal port. Unlike the prior art, the adaptor body is made of a flexible, preferably resilient, material such as silicone or polyvinyl chloride with sufficient plasticizers added to impart flexibility.

Rather than requiring instruments to bend or rotating barrels into and out of position, the adaptor body allows the clinician to align the desired proximal port with the distal port simply by manipulating the adaptor body. Such manipulation requires little additional dexterity because it is common practice for the clinician to hold the proximal end of the endotracheal tube, or the adaptor itself, when performing a procedure.

In accordance with one aspect of the invention, the adaptor body is formed as an offset wye, with the two proximal channels being axially offset approximately 30 degrees. One of the proximal channels may be configured for attachment to a "permanent" device, such as a closed suction catheter assembly, while the other channel would be configured for use with a "temporary" device, such as a bronchoscope. When an instrument is advanced through one of the proximal channels, it would be in alignment with the distal channel without any manipulation of the adaptor body. If the other proximal channel were used, it could be placed in alignment with the distal channel by manipulating the proximal end of the adaptor body into a desired position which is 30 degrees offset from the original position.

In accordance with another aspect of the invention, a wye could be formed with each of the proximal channels being offset by the same amount, i.e. 15 degrees. By slightly manipulating the adaptor body, either of the proximal channels could be placed in alignment with the distal channel.

In accordance with still yet another aspect of the present invention, the adaptor body could be made with three or more proximal channels. By manipulating the adaptor body, any of the proximal channels could be substantially aligned with the distal channel.

In accordance with still yet another aspect of the present invention, the adaptor body could be made of a rigid material which is attached to a flexible joint or material, such as a popoid cylinder which would allow the adaptor body to pivot in the position necessary to place a desired proximal channel in alignment with the distal channel.

In accordance with still another aspect of the present invention, a retaining mechanism may be provided adjacent the adaptor body. The retaining mechanism would allow the resilient adaptor body to be held in a position in which a desired proximal channel is aligned with the distal channel to facilitate conducting a procedure through that proximal channel. Once completed, the retaining mechanism could be released and the adaptor body returned to its normal position.

In accordance with still yet another aspect of the present invention, one or more of the proximal channels can have a sealing mechanism disposed therein to maintain positive end expiratory, pressure (PEEP) regardless of whether the proximal channel is being used for a procedure.

BRIEF DESCRIPTION OF THE DRAWINGS

The above and other objects, features and advantages of the invention will become apparent from a consideration of the following detailed description presented in connection with the accompanying drawings in which.

DETAILED DESCRIPTION

Reference will now be made to the drawings in which the various elements of the present invention will be given numeral designations and in which the invention will be discussed so as to enable one skilled in the art to make and use the invention. It is to be understood that the following description is only exemplary of the principles of the present invention, and should not be viewed as narrowing the pending claims.

Figure 1A:
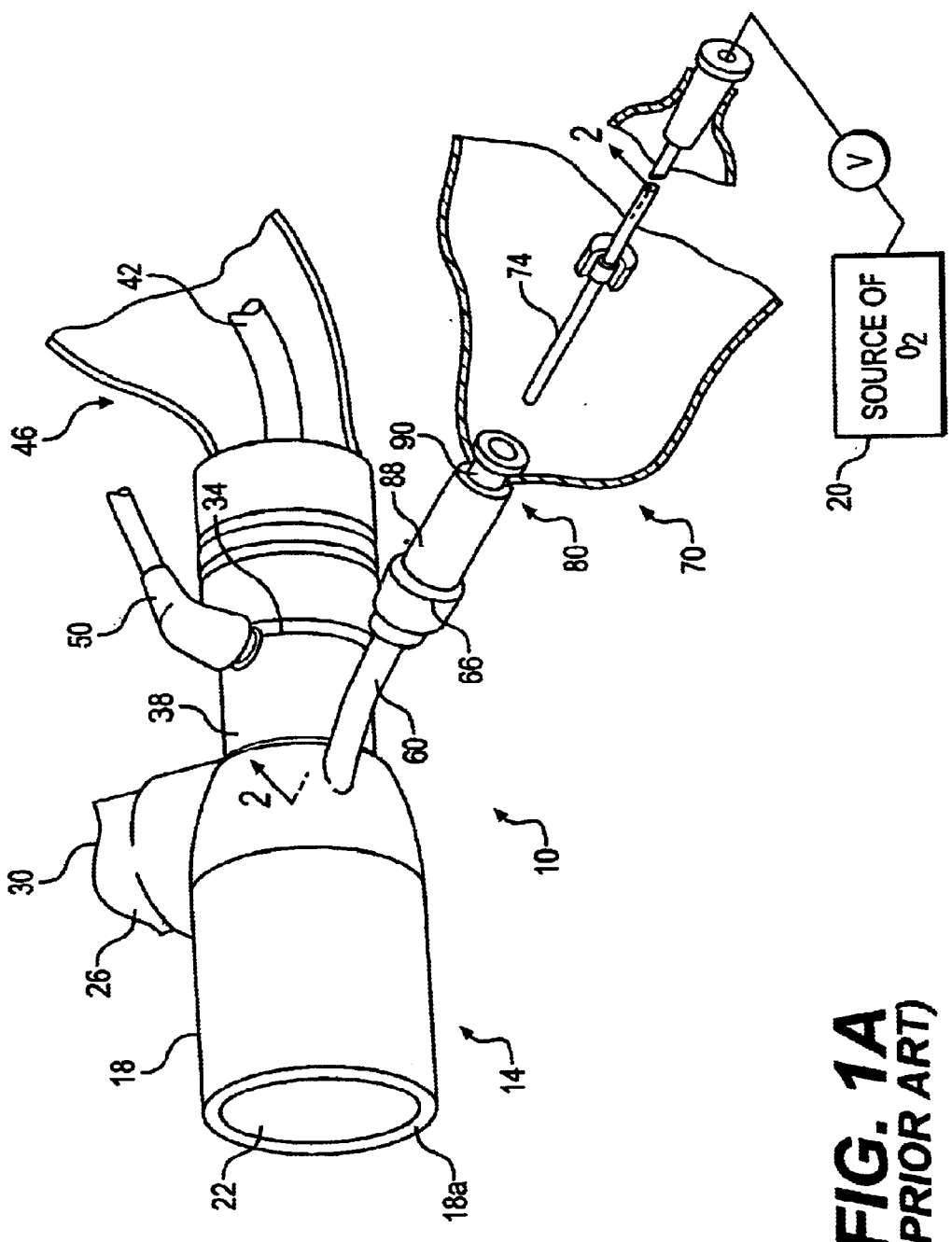
FIG. 1A shows a perspective, partially fragmented view of a multiple port adaptor made in accordance with the teachings of the prior art.
Figure 1B:
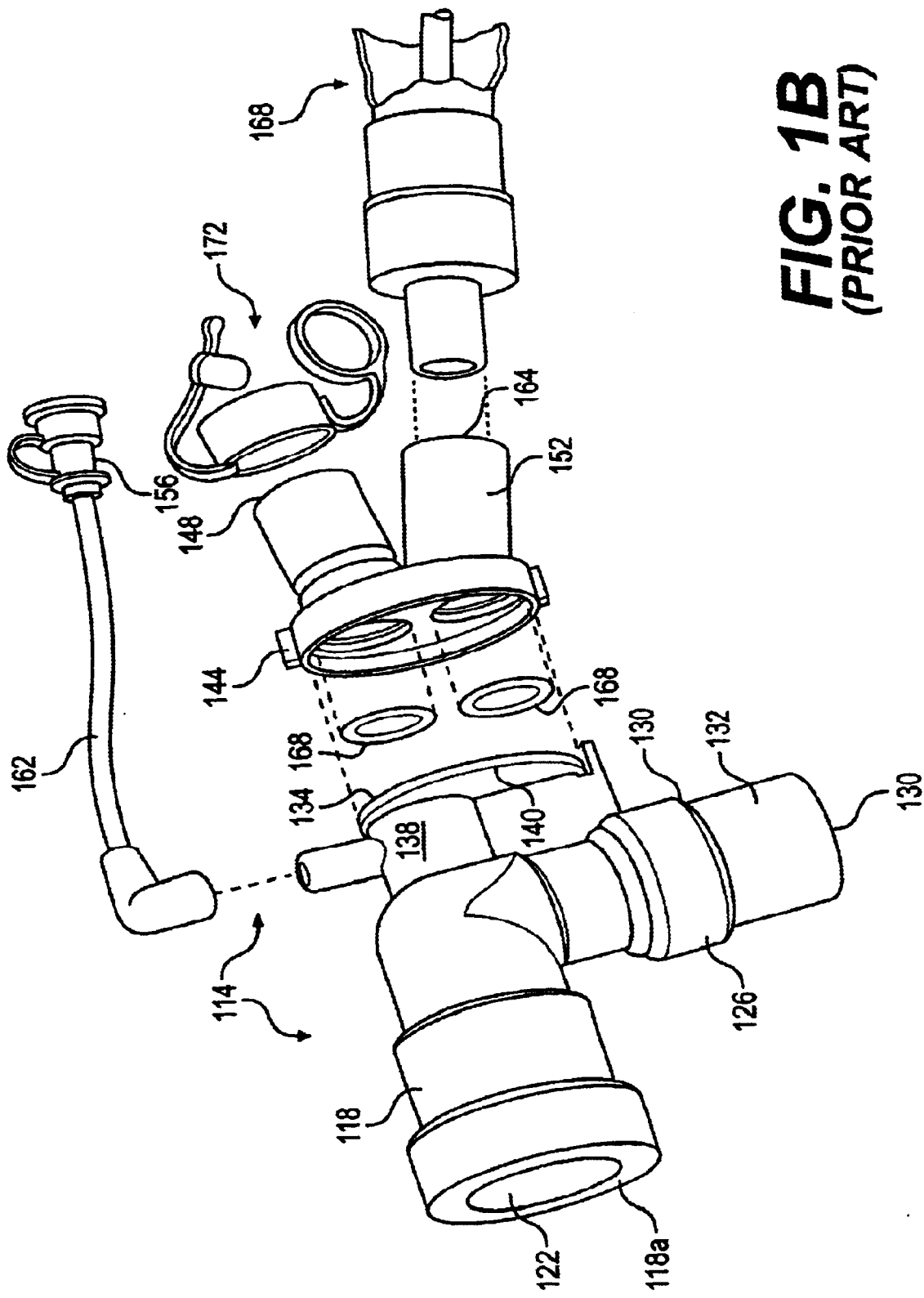
FIG. 1B shows a perspective, partially exploded view of another multiple port adaptor made in accordance with the teachings of the prior art.
Figure 2A:
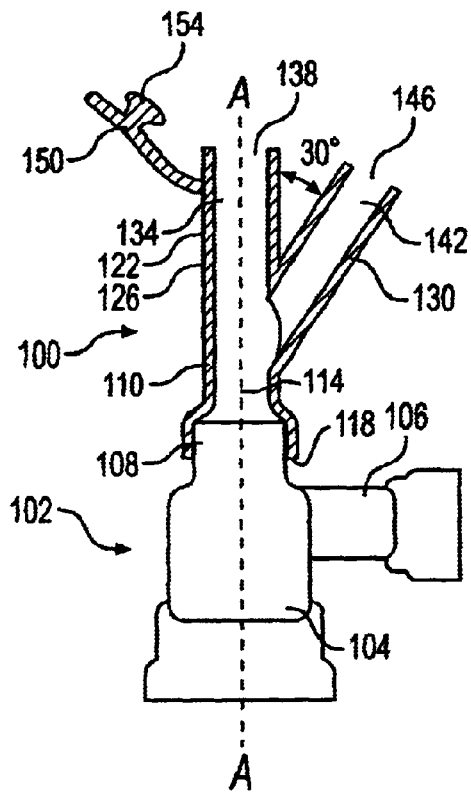
FIG. 2A shows a cross-sectional view of a flexible multiple port adaptor in accordance with the teachings of the present invention, the adaptor being in an unbiased position in which a first proximal channel is in alignment with a distal channel of the adaptor.

Referring to FIG. 2A, there is shown a cross-sectional view of an adaptor body, generally indicated at 100. The adaptor body is attached to the proximal end of a conventional T-fitting, generally indicated at 102, which includes a distal barrel 104 for attachment to an endotracheal tube, a lateral barrel 106 for attachment to ventilation tubing, and a proximal barrel 108 for attachment to some instrument which may be advanced through the T-fitting 102 and into the endotracheal tube. (It will be appreciated by those skilled in the art that the adaptor body can be connected to a T-fitting or directly to an endotracheal tube depending on the particular needs of the patient.)

The adaptor body 100, includes a distal portion 110 which is formed as a first, distal barrel defining a distal channel 114 which is configured for the passage of medical instruments therethrough. At the distal end of the barrel is a distal port 118 which is configured for receiving the proximal end of either a T-fitting 102 or an endotracheal tube. The proximal ends of endotracheal tubes are typically of a standardized exterior diameter so that devices of different manufacturers may be readily attached thereto. Thus, exact dimensions are not provided.

The adaptor body 100 also includes a proximal portion 122 which defines a Wye having a first proximal barrel 126 and a second proximal barrel 130. As shown in FIG. 2A, the barrel 126 of the proximal portion 122 defines a first proximal channel 134 which is in axial alignment with the distal channel 114 defined by the distal portion 110 as indicated by line A—A. The second proximal channel 134 terminates in a first proximal port 138 which is configured to receive a medical instrument.

The second barrel 130 defines a second proximal channel 142 which is offset from the axis A—A at an angle of approximately 30 degrees. A second proximal port 146 is formed by the barrel 130 at the proximal end of the second proximal channel 142.

One or both of the barrels 126 and 130 may have a cap 150 attached thereto. The cap 150 has a nub 154 which is configured for sealing the port (138 or 146) closed when the port is not in use. Thus, the assembly body 100 will typically have a cap 150 for the proximal port which is intend for use with temporary instruments, such as a bronchoscope, which are used for a short period of time. A cap may be omitted for ports which are intended for use with permanent instruments, such as closed suction catheters which will typically be left in place for prolonged periods of time. Thus, as shown in FIG. 2A, a closed suction catheter would typically be connected to port 146 when the adaptor body 100 is placed in use. The cap 150 would be used to cover port 138 until it is needed. Not only does the cap 150 preserve PEEP, it also helps prevent patient secretions from contacting the clinician and vice-versa.

Figure 2B:
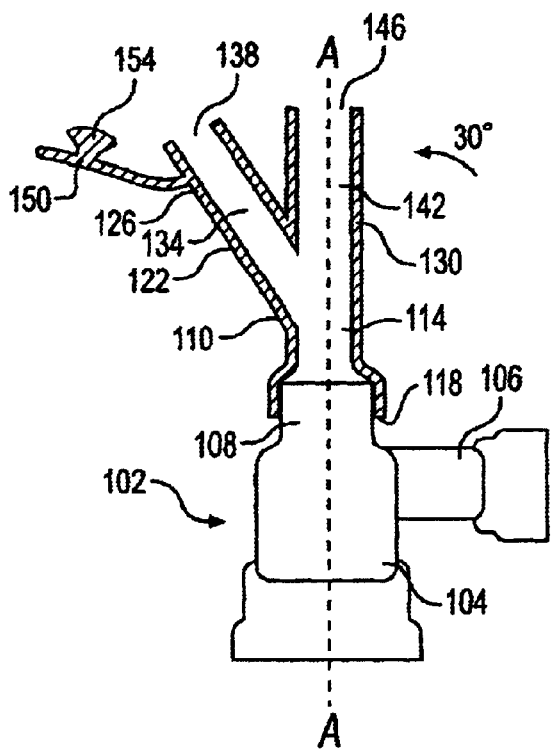
FIG. 2B shows a cross-sectional view of the flexible multiple port adaptor of FIG. 2A, with the adaptor being forced into a second position to align a second proximal channel with the distal channel.

While FIG. 2A shows the adaptor body in a first, resting position, FIG. 2B shows a cross-sectional view of the adaptor body 100 in a second position wherein the proximal portion 122 has been pivoted 30 degrees to move the second proximal channel 142 into axial alignment with the distal channel 114. The adaptor body 100 is typically formed from a flexible, resilient material such as silicone or polyvinyl chloride with sufficient plasticizers to make it flexible. In one embodiment of the present invention, the plasticizers are butadiene polymers. The flexibility of the adaptor body 100 enables the clinician to manipulate the proximal portion 122 into position to provide the desired alignment between the distal channel 114 and either of the proximal channels 134 or 142. Because the clinician typically holds the T-fitting 102 to prevent unnecessary torque on the patient's endotracheal tube, the clinician can use his or her hand to bend the proximal portion 122 of the adaptor body 100 until the desired proximal channel is in axial alignment with the distal channel 114.

Once the second proximal channel 142 is pivoted into axial alignment with the distal channel 114, the clinician can freely advance a medical instrument through the second proximal port 146 and through the adaptor body 100. Because the channels 114 and 142 are in alignment, the medical instrument does not need to bend upon entry into the endotracheal tube. This, in turn, facilitates advancement of the instrument, obviates mechanical and optical distortion of instruments such as bronchoscopes, and decreases the risk of the instrument wiping mucus or other secretions on the sides of the T-fitting 102 of the adaptor body 100 as it is withdrawn from the endotracheal tube.

Figure 3A:
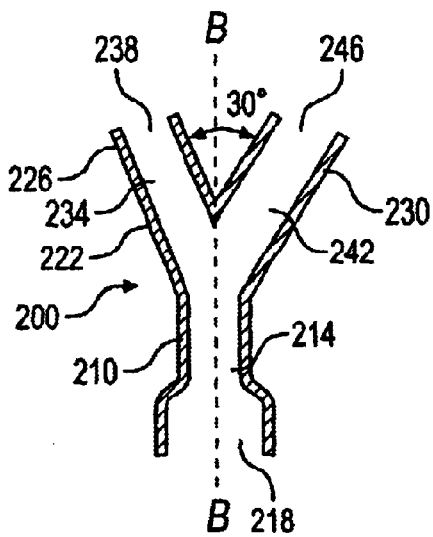
FIG. 3A shows a cross-sectional view of another configuration of a flexible multiple port adaptor in which neither of two proximal channels is in substantial alignment with the distal channel when the adaptor is at rest.

FIG. 3A shows a cross-sectional view of another configuration of a flexible multiple port adaptor. The adaptor includes an adaptor body, generally indicated at 200, with a distal portion 210. The distal portion 210 includes a barrel defining a distal channel 214 and a distal port 218 at the distal end. The adaptor body 210 also includes a proximal portion 222 with a first proximal barrel 226 and a second proximal barrel 230. As with the previous embodiment, the first proximal barrel 226 defines a first proximal channel which terminates at a proximal port 238. Likewise, the second proximal barrel 230 defines a second proximal channel 242 and ends at a second proximal port 246.

The embodiment of FIG. 3A is different from FIGS. 2A and 2B in that neither of the proximal channels 234 or 242 is in substantial axial alignment with the distal channel 214 (represented by line B—B) when the adaptor is in the first, resting position. Rather, the proximal channels 234 and 242 are offset from each other by approximately 30 degrees and from the axis B—B by approximately 15 degrees.

In order to advance a medical instrument through one of the proximal channels 234 or 242 and the distal channel 214, the proximal portion 222 is pivoted into a second position so that the desired proximal channel is in axial alignment with the distal channel. Thus, as shown in FIG. 3B, the proximal portion 222 has been pivoted approximately 15 degrees so that the second proximal channel 242 is disposed in substantial alignment with the distal channel 214.

Figure 3B:
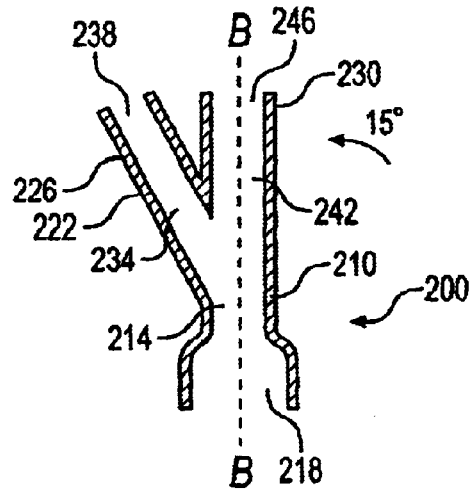
FIG. 3B shows a cross-sectional view of the embodiment of FIG. 3A, wherein the adaptor body has been manipulated to align one of the proximal channels with the distal channel.

While the embodiment of FIGS. 3A and 3B lacks the advantage of having one proximal channel 234 or 242 in alignment with the distal channel 214 when in a resting state, it provides the advantage of requiring only a slight amount of deflection to align the desired proximal channel with the distal channel so that a medical instrument can be advanced without bending.

Figure 4A:
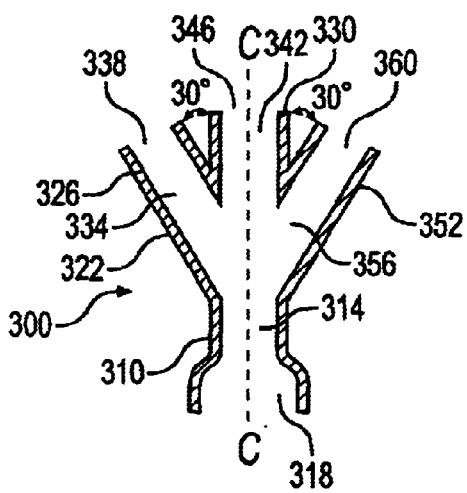
FIG. 4A shows a cross-sectional view of yet another embodiment wherein three proximal channels are provided so as to be alignable with a single distal channel in accordance with the teachings of the present invention.
Figure 4B:
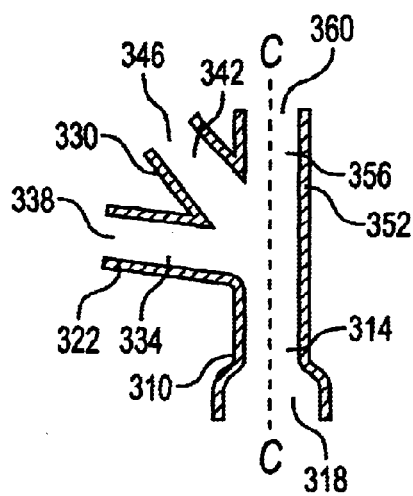
FIG. 4B shows the embodiment of FIG. 4A manipulated so that one of the proximal channels is in alignment with the distal channel.

Turning now to FIGS. 4A and 4B, there is shown a cross-sectional view of yet another embodiment of a flexible multiple port adaptor made in accordance with the principles of the present invention. The adaptor is formed of an adaptor body, generally indicated at 300. The adaptor body 300 includes a distal portion 310 which defines a distal channel 314 and a distal port 318. The adaptor body also includes a proximal portion 322 which has a first barrel 326 defining a first proximal channel 334 and a first proximal port 338, a second barrel 330 defining a second proximal channel and a second proximal port 346, and a third barrel 352 defining a third proximal channel 356 and a third proximal port 360.

As shown in FIG. 4A, the first, second and third barrels 326, 330 and 352, respectively, are disposed along a common plane. Each of the barrels 326, 330 and 352 are disposed approximately 30 degrees from the adjacent barrel to provide sufficient working room to use any instrument in the barrel, while keeping the barrels sufficiently close that excessive bending of the adaptor body 300 is avoided.

Turning specifically to FIG. 4B, there is shown a cross-sectional view of the adaptor body 300 with the proximal portion 320 being pivoted into a second position 30 degrees to the left. The third proximal barrel 352 is oriented so that the third proximal channel 356 is in axial alignment with the distal channel 314 as represented by line C—C. The adaptor body 300 could also be pivoted 30 degrees in the opposite direction to place the first barrel 326 and first proximal channel 334 in axial alignment with the distal channel 314. Thus, such a configuration enables the clinician to use three different medical instruments without bending any of the instruments and without removing the instrument from attachment to the adaptor body. This, in turn, decrease the risk of nosocomial infections and exposure of clinicians to body secretions.

Figure 5:
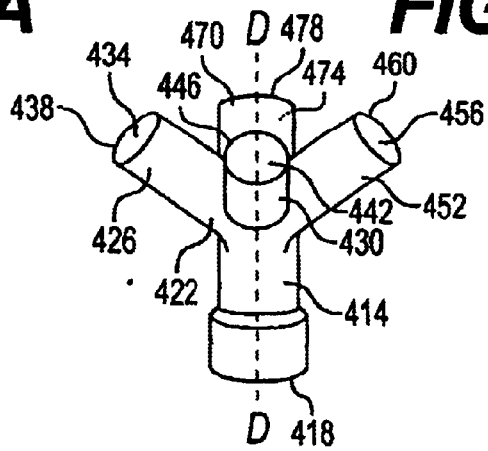
FIG. 5 shows a perspective view of yet another embodiment of a flexible multiple port adaptor in accordance with the teachings of the present invention.

While the embodiments of the present invention shown in FIGS. 2A through 4B show a plurality of barrels being disposed in a common plane, FIG. 5 shows a perspective view of yet another embodiment of a flexible multiple port adaptor in which a plurality of barrels extend threedimensionally. The adaptor of FIG. 5 includes an adaptor body, generally indicated at 400, which has a distal portion 410 defining a distal channel 414 and a distal port 418.

The adaptor body 400 also includes a proximal portion 422. The proximal portion 422 includes a first proximal barrel 426 and a second proximal barrel 430. The first proximal barrel 426 defines a first proximal channel 434 and a first proximal port 438. The second proximal barrel 430 defines a second proximal channel 442 and a second proximal port 446. Rather than being offset from one another 30 degrees in a common plane, the first and second barrels 426 and 430 are each offset from the axis of the distal channel 314 approximately 30 degrees and are offset from one another approximately 90 degrees.

The proximal portion 422 of the adaptor body 400 also includes a third barrel 452 defining a third proximal channel 456 and a third proximal port 460, and a fourth barrel 470 defining a fourth proximal channel 474 and a fourth proximal port 478. Both the third barrel 452 and the fourth barrel 470 are disposed at an angle of about 30 degrees from the axis D—D of the distal channel 414 and are disposed approximately 90 degrees from the barrels on either side. By pivoting the proximal portion 30 degrees anyone of the proximal channels 434, 442, 452 and 474 can be aligned with the distal channel 414.

While FIGS. 4A through 5 show proximal barrels which are evenly spaced from one another, those skilled in the art will appreciate that the barrels could be unevenly spaced to improve access for certain instruments. Likewise, the size of the proximal channels 426, 442, 452 and 474 need not be the same. Some medical instruments can use a smaller port, thereby allowing some other port to be enlarged.

Figure 6A:
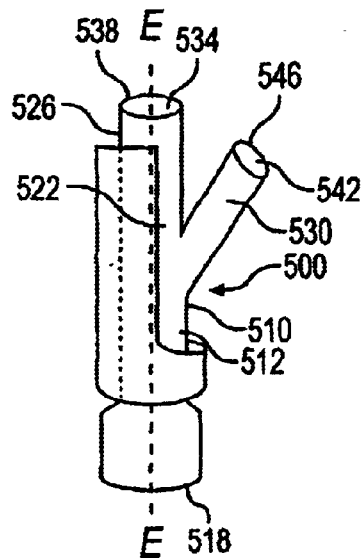
FIG. 6A shows a side view of a flexible multiple port adaptor having a retaining mechanism in accordance with one of the principles of the present invention, the retaining mechanism being in an off position.
Figure 6B:
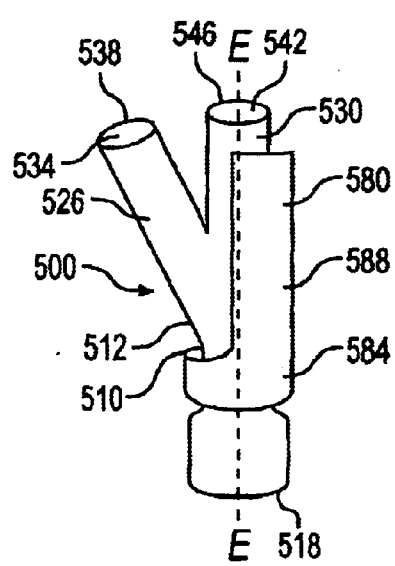
FIG. 6B shows a side view of the embodiment shown in FIG. 6A, with the retaining mechanism in an on position wherein the retaining mechanism holds the flexible multiple port adaptor out of its normal position.

Turning now to FIGS. 6A and 6B, there is shown yet another aspect of the present invention. While it is relatively easy to pivot the proximal portion of the adaptor body so that the desired proximal channel is aligned with the distal channel, there are times when the clinician may not want to have to hold the adaptor body in place. Such a situation may include the use of a medical instrument which must be delicately handled, or which requires the use of both hands.

FIGS. 6A and 6B show an adaptor body, generally indicated at 500, which includes a distal portion 510 having a distal barrel 512 defining a distal channel and a distal port 518. The adaptor body 500 also includes a proximal portion 522 having a first proximal barrel 526 and a second proximal barrel 530. The first proximal barrel 526 defines a first proximal channel 534 and a first proximal port 538. The second proximal barrel 530 defines a second proximal channel 542 and a second proximal port 546.

Disposed about the distal barrel 512 and extending upwardly adjacent the proximal portion 522 is a retaining mechanism, generally indicated at 580. The retaining mechanism 580 is preferably formed of a lightweight plastic with sufficient rigidity to counter the natural bias of the adaptor body 500 into its first, resting position. The lower portion 584 of the retaining mechanism 580 forms a ring (or a substantial portion of a ring) to engage the distal barrel 512 and hold an upper portion 588 of the retaining mechanism in an orientation generally parallel with the axis E—E passing through the distal barrel.

The distal portion 584 of the retaining mechanism 580 is rotatable about the distal barrel 512 so that the proximal portion 588 of the retaining mechanism can be disposed adjacent either the first barrel 526 or the second barrel 530. As shown in FIG. 6A, the proximal portion 588 of the retaining 20 mechanism 580 applies no force to the proximal portion 522 because the first barrel 526 is normally disposed in axial alignment with the distal barrel 512. Thus, procedures can be performed through the second port 538 without need to displace the proximal portion 522 of the adaptor body 500.

When the clinician desires to perform a procedure through the second proximal port 546, the retaining mechanism 580 is rotated so that the proximal portion 588 of the retaining mechanism applies a force against the second proximal barrel 530, forcing the second proximal barrel into substantial alignment with the distal barrel 512 as shown in FIG. 6B As long as the retaining mechanism 580 remains in the position shown in FIG. 6B, the second proximal barrel 530 is displaced into alignment with the distal barrel 512—thereby allowing a procedure to be carried out through the second proximal port 546 without the clinician holding the adaptor body 500.

While shown in FIGS. 6A and 6B as being used with an offset Wye configuration, those skilled in the art will appreciate that such a retaining mechanism can be used with several different adaptor bodies. For example, the retaining mechanism 580 shown in FIGS. 6A and 6B could be used with the adaptor body 200 as shown in FIGS. 3A and 3B to alternatingly move either of the proximal barrels 226 and 230 and thus the channels 234 and 242 into alignment with the distal channel 214. Likewise, the retaining mechanism 580 could be used with the adaptor body 300 shown in FIGS. 4A and 4B. When the proximal portion 588 of the retaining mechanism 580 is disposed on the front or back of the adaptor body 300, the adaptor body would maintain the configuration shown in FIG. 4A. If the proximal portion 588 of the retaining mechanism 580 were rotated to the right side, the adaptor body 300 would be held in the configuration shown in FIG. 4B. Rotating the proximal portion 588 to the left side would provide the mirror image of the configuration shown in FIG. 4B.

Figure 6C:
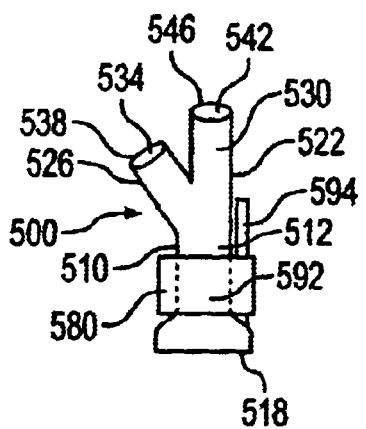
FIG. 6C shows a side view of another configuration of a retaining mechanism disposed on a flexible multiple port adaptor in accordance with the teachings of the present invention.
Figure 6D:
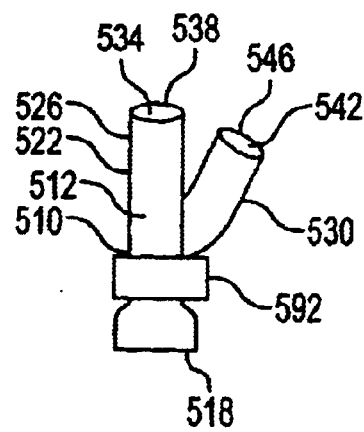
FIG. 6D shows a side view of the embodiment shown in FIG. 6C, which the retaining mechanism is in the on position.

FIGS. 6C and 6D show another configuration of a retaining mechanism 580 for use with the adaptor body 500. The retaining mechanism 580 includes a ring 592 disposed about the distal barrel 512, and a slide 594 slidably engaged with the ring. When the slide 594 is extended proximally, it engages the second proximal barrel 530 and causes the proximal portion 522 to pivot so that the second proximal barrel 530 and the distal barrel 512 are in alignment. When the slide 594 is retracted distally, the adaptor body 500 returns to its normal position with the first proximal barrel 526 in alignment with the distal barrel 512 as shown in FIG. 6D.

Figure 6E:
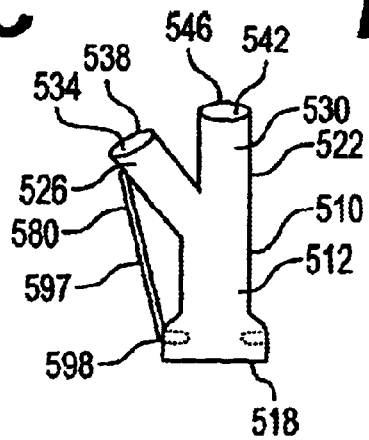
FIG. 6E shows yet another embodiment of a retaining mechanism for a flexible multiple port adaptor in accordance with the teachings of the present invention.

FIG. 6E shows yet another embodiment of the retaining mechanism 580. The retaining mechanism 596 includes a strap 597 which is attached to the first proximal barrel 526. When the strap 597 is pulled down into engagement with a fastener 598 on the distal portion 510 of the adaptor body 500, the first proximal barrel 526 is pulled out of alignment with the distal barrel 512, and the second proximal barrel 530 is moved into alignment. Once the fastener 598 is released, the adaptor body 500 returns to its original position in which the first proximal barrel 526 is in alignment with the distal barrel 512.

Figure 7A:
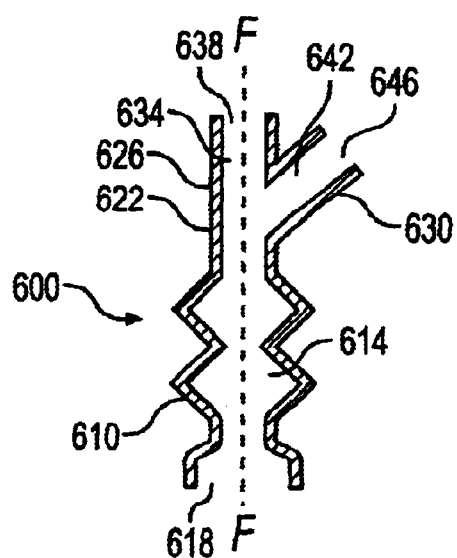
FIG. 7A shows a side cross-sectional view of another embodiment of a flexible multiple port adaptor having a popoid segment in accordance with the teachings of the present invention to facilitate selective alignment between the proximal channels and the distal channel of the adaptor.
Figure 7B:
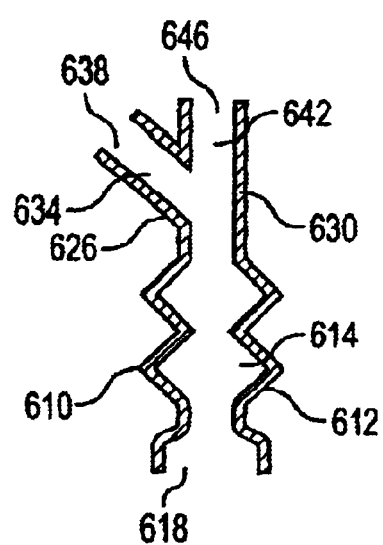
FIG. 7B is a cross-sectional view of the embodiment in FIG. 7A, with the popoid segment being bent to change the alignment between the proximal channels and the distal channel.

Turning now to FIGS. 7A and 7B, there is shown yet another configuration of a flexible multiple port adaptor. The adaptor includes an adaptor body 600 with a distal portion 610 defining a distal channel 614 and a distal port 618. Rather than a conventional barrel shape, the distal portion 610 has an accordion-like popoid segment 612. Those skilled in the art will appreciate that popoid segments are commonly used in the medical field. The popoid is formed from tapered annular walls which allow walls to compress and extend in a similar manner to an accordion. Because one side can extend while an opposing side is being compressed, a popoid can allow considerable bending of a segment without causing it to collapse on a channel 614 extending therethrough.

FIG. 7A shows the popoid segment 612 in its original position. When used with an offset wye, the first proximal channel 634 formed by the first proximal barrel 626 of the proximal portion 622 is in axial alignment with the distal channel 614 as indicated by line F—F.

The popoid segment 610 may be bent, however, to place the second proximal channel 642 defined by the second proximal barrel 630 into alignment with the distal channel 514. This can be accomplished by either compressing the left side of the popoid (relative to FIGS. 7A and 7B) or by extending the right side, depending on whether the popoid is expanded or compressed. The popoid segment 612 will tend to hold this position until it is adjusted again.

While the previous embodiments would typically be formed from a single molded piece of flexible plastic, the complexities of forming a true popoid would make it much easier to form a relatively rigid proximal portion 622 and then attach the popoid distal portion 610. The two could be attached by heat sealing, by an adhesive or by other methods known to those skilled in the art. (Of course, a similar approach could be used with the prior embodiments so that rigid proximal barrels could be used if necessary.) A popoid-like configuration could be provided, however, by providing a sidewall made of semi-rigid plastic with a plurality of thinned wall sections to impart the desired flexibility.

Regardless of which configuration is used, a clinician can perform procedures through the first proximal port 638 or the second proximal port 646 simply by pivoting the popoid segment 612 to align the proper channel in the proximal portion 622 with the distal channel 614. If a true popoid is used, the popoid will typically hold that position until the clinician reorients the popoid again.

Figure 8:
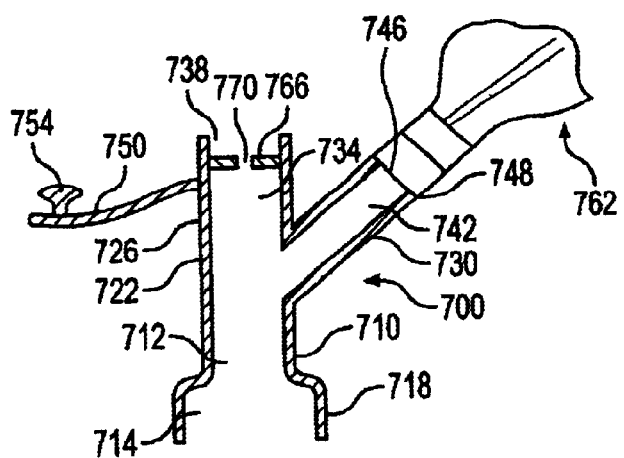
FIG. 8 is a cross-sectional view of yet another embodiment of a flexible multiple port adaptor having a positive end expiratory pressure seal formed therein in accordance with the present invention.

FIG. 8 is a cross-sectional view of yet another embodiment of a flexible multiple port adaptor. The adaptor includes an adaptor body, generally indicated at 700. The adaptor body has a distal portion 710 with a distal barrel 712 defining a distal channel 714 and a distal port 718. The adaptor body also includes a proximal portion 722 with a first proximal barrel 726 defining a first proximal channel 734 and first proximal port 738, and a second proximal barrel 730 defining a second proximal channel 742 and a second proximal port 746.

In use, the adaptor body 700 will typically have a relatively permanent device, i.e. a device which may stay in for hours or some other prolonged period, disposed in one port, leaving the other port for devices which will be used for a brief period. Thus, for example, a closed suction catheter 762 may be placed in the second proximal port 748. This leaves the first proximal port 738 available for use.

When the first proximal port 738 is not being used, it will typically be covered by a cap 750 with a nub 754 for sealing the port. During use, however, it is important to maintain positive end expiratory pressure (PEEP) for the patient. Failure to maintain PEEP can cause serious respiratory problems for the patient.

When the first proximal port 738 is being used by a medical instrument, PEEP may be maintained by placing an elastomeric or other seal 766 with a small hole 770 in the first proximal channel 734. The seal 766 surrounds the medical instrument being passed through the hole 770 to prevent air from escaping from the respiratory circuit by way of the adaptor body 700. The seal 766 also helps to inhibit the flow of bacteria and other contaminants from the patient to the clinician and vice-versa.

Those skilled in the art will appreciate that, while the PEEP seal 766 could be molded integrally with the adaptor body, such a configuration would result in a complex mold. Thus, it is equally feasible to simply form the PEEP seal 766 separately and then secure it to the adaptor body 700. If desired, each of the proximal channels could have a PEEP seal 766.

Figure 9A:
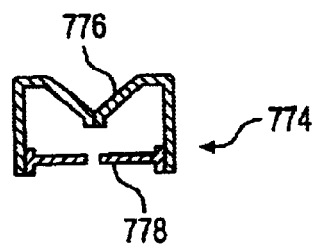
FIGS. 9A through 9C are cross-sectional views of seals which may be used to maintain positive end expiratory pressure in the flexible multiple port adaptor.
Figure 9B:
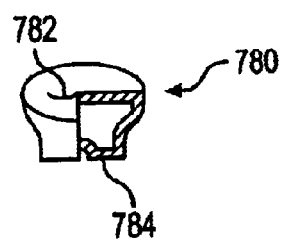
Figure 9C:
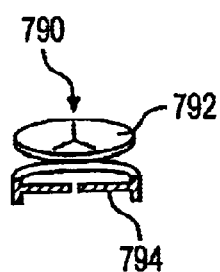

FIGS. 9A through 9C are cross-sectional and partial cross-sectional views of seals which may be used to maintain positive end expiratory pressure in the flexible multiple port adaptor and prohibit foreign matter from access to the patient and to retain potentially infectious agents within the patient circuit. FIG. 9A shows a duckbill closure seal, generally indicated at 774. The closure seal 774 has an upper duckbill valve 776 such as are well known in the art, in combination with a disk 778 forming a PEEP seal. Preferably, two sealing members 776 and 778 are provided to prevent tidal volume loss because a single seal will often not completely close about the introduced device. Additionally, the second seal provides yet another barrier against patient mucus contacting the clinician.

FIG. 9B is a partial cross-sectional view of a closure seal 780. The one-piece closure seal 780 includes an upper slit seal 782, and a lower PEEP seal 784. The upper and lower seals 782 and 784 work together to maintain tidal volumes within the patient's ventilation circuit regardless of whether an instrument is being advanced through the closure seal 780.

Such a seal is disclosed in U.S. Pat. No. 4,351,328 to Bodai.

FIG. 9C show yet another closure seal, generally indicated at 790. The closure seal 790 includes an upper slit valve 792 and a lower PEEP seal 794. The slit valve 792 is placed on top of the PEEP seal 794 to provide an integrated seal configured to prevent any substantial loss of air from the patient's ventilation circuit.

Thus there is disclosed an improved flexible multiple port adaptor. Those skilled in the art will appreciate numerous modifications which can be made without departing from the scope and spirit of the present invention. The appended claims are intended to cover such modifications.

What is claimed is:

1. A multiple port adaptor assembly for use with endotracheal medical instruments, the multiple port adaptor assembly comprising:

an adaptor body having a distal portion defining a distal channel and a proximal portion defining at least a first proximal channel and a second proximal channel with at least one of said proximal channels being normally out of axial alignment with the distal channel, and wherein the proximal portion is configured for pivoting to move the at least one of said proximal channels into axial alignment with the distal channel; and said distal portion further comprising a distal port configured for receipt of an end of a separately formed fitting, said adaptor formed of a flexible material such that said proximal portion is pivotal with respect to said distal portion and fitting.

2. A multiple port adaptor assembly according to claim 1, wherein the first proximal channel is normally in alignment with the distal proximal channel, and wherein the proximal portion may be pivoted to move the second proximal channel into alignment with the distal channel.

3. A multiple port adaptor assembly according to claim 1, wherein the first proximal channel and the second proximal channel are axially offset from one another by at least 30 degrees.

4. A multiple port adaptor assembly according to claim 1, wherein the first and second proximal channels each have a central axis, and wherein the central axis of each channel is offset from a central axis of the distal channel.

5. The multiple port adaptor assembly according to claim 1, wherein the adaptor body is formed from silicone.

6. The multiple port adaptor assembly according to claim 1, wherein the adaptor body is formed from polyvinyl chloride having sufficient plasticizers to render the polyvinyl chloride flexible.

7. The multiple port adaptor assembly according to claim 6, wherein the plasticizers comprise butadiene polymers.

8. The multiple port adaptor assembly according to claim 1, wherein the adaptor body further comprises a third proximal channel which is offset from the first proximal channel and the second proximal channel, and wherein the third proximal channel may be displaced into alignment with the distal channel by movement of the proximal portion of the adaptor body.

9. The multiple port adaptor assembly according to claim 8, wherein the adaptor body includes a fourth proximal channel movable between a first position wherein the fourth proximal channel is out of axial alignment with the distal channel and a second position wherein the fourth proximal channel is disposed in axial alignment with the distal channel.

10. The multiple port adaptor assembly according to claim 8, wherein the first proximal channel, the second proximal channel and the third proximal channel are disposed in a common plane.

11. The multiple port adaptor assembly according to claim 1, wherein the adaptor body comprises a popoid disposed so as to facilitate pivoting of the proximal portion to thereby selectively align the first proximal channel and the second proximal channel with the distal channel.

12. The multiple port adaptor assembly according to claim 1, wherein at least one of the first proximal channel and the second proximal channel has a seal disposed therein.

13. The multiple port adaptor assembly according to claim 12, wherein the seal comprises a PEEP seal.

14. The multiple port adaptor assembly according to claim 12, wherein the seal comprises a duck bill valve.

15. The multiple port adaptor assembly according to claim 12, wherein the seal comprises a slit valve.

16. A multiple port adaptor assembly for use with endotracheal medical instruments, the multiple port adaptor comprising:
    an adaptor body having a distal portion defining a distal channel and a proximal portion defining at least a first proximal channel and a second proximal channel with at least one of said proximal channels being normally out of axial alignment with the distal channel, and wherein the proximal portion is configured for pivoting to move the at least one of said proximal channels into axial alignment with the distal channel; and
    a retaining member for holding a desired proximal channel of the adaptor body in axial alignment with the distal channel.

17. The multiple port adaptor assembly according to claim 16, wherein the retaining member comprises a distal portion disposed about the distal portion of the adaptor body, and a proximal portion extending proximally from the distal portion.

18. The multiple port adaptor assembly according to claim 17, wherein the proximal portion comprises a slide.

19. The multiple port adaptor assembly according to claim 16, wherein the retaining member comprises a strap attached to the proximal portion of the adaptor body and attachable to the distal portion of the adaptor body.

20. A multiple port adaptor assembly comprising an adaptor body having:
    a distal portion having a distal barrel defining a distal channel and a distal port configured for attachment to an endotracheal tube adaptor;
    a proximal portion having a first proximal barrel defining a first proximal channel and a second proximal barrel defining a second proximal channel, at least one of the first proximal channel and, the second proximal channel being out of axial alignment with the distal channel;
    wherein the proximal portion is pivotable to move the first proximal channel and the second proximal channel and to move the at least one of the first proximal channel and the second proximal channel into axial alignment with the distal channel; and
    wherein said distal port is configured for receipt of an end of a separately formed fitting on the endotracheal tube adaptor, said adaptor body being at least partially formed of a flexible material such that said proximal portion is pivotable with respect to said distal portion and fitting.

21. The multiple port adaptor assembly according to claim 20, wherein at least a portion of the adaptor body is formed from silicone.

22. The multiple port adaptor assembly according to claim 20, wherein at least a portion of the adaptor body is formed from polyvinyl chloride having sufficient plasticizers to impart flexibility.

23. The multiple port adaptor assembly according to claim 20, wherein at least a portion of the adaptor body is formed with a flexible joint.

24. The multiple port adaptor assembly according to claim 23, wherein the flexible joint is formed by a popoid.

25. The multiple port adaptor assembly according to claim 20, wherein at least a portion of the adaptor body is formed with a shape-retaining flexible portion.

26. The multiple port adaptor assembly according to claim 20, wherein both the first proximal channel and the second proximal channel are out of axial alignment with the distal channel.

27. The multiple port adaptor assembly according to claim 20, wherein at least one of the first proximal channel and the second proximal channel has a seal disposed therein.

28. The multiple port adaptor assembly according to claim 27, wherein the seal comprises a PEEP seal.

29. The multiple port adaptor assembly according to claim 27, wherein the seal comprises a duckbill valve.

30. The multiple port adaptor assembly according to claim 27, wherein the seal comprises a slit valve.

31. The multiple port adaptor assembly according to claim 27, wherein the seal comprises a PEEP seal and a valve selected from the group consisting of a duckbill valve and a slit valve.

32. The multiple port adaptor assembly according to claim 27, further comprising a cap for covering the seal.

33. The multiple port adaptor assembly according to claim 20, wherein the adaptor body further comprises a third proximal channel, and wherein at least two of the three proximal channels are not disposed in axial alignment with the distal channel when the adaptor body is in a resting state, but may be pivoted into alignment with the distal channel by manipulation of the adaptor body.

34. A multiple port adaptor assembly comprising an adaptor body having:
  a distal portion having a distal barrel defining a distal channel and a distal port configured for attachment to an endotracheal tube adaptor;
  a proximal portion having a first proximal barrel defining a first proximal channel and a second proximal barrel defining a second proximal channel, at least one of the first proximal channel and the second proximal channel being out of axial alignment with the distal channel; and
  wherein the proximal portion is pivotable to move the first proximal channel and the second proximal channel and to move the at least one of the first proximal channel and the second proximal channel into axial alignment with the distal channel;
  wherein the adaptor body is movable between a first position, wherein the adaptor is at rest, and a second position wherein one of the proximal channels which is not disposed in axial alignment with the distal channel when the adaptor body is at rest is moved into axial alignment with the distal channel, and wherein the adaptor further comprises a retention mechanism for holding the adaptor body in the second position.

35. A multiple port adaptor assembly comprising an adaptor body having:
  a distal portion having a distal barrel defining a distal channel and a distal port configured for attachment to an endotracheal tube adaptor;
  a proximal portion having a first proximal barrel defining a first proximal channel and a second proximal barrel defining a second proximal channel, at least one of the first proximal channel and the second proximal channel being out of axial alignment with the distal channel when the adaptor body is at rest;
  wherein at least a portion of the adaptor body is formed from a sufficiently flexible material to enable pivoting of an axis of the proximal portion relative to a central axis of the distal portion; and
  wherein said distal port is configured for receipt of an end of a separately formed fitting of the endotracheal tube adaptor, said adaptor body being at least partially formed of a flexible material such that said proximal portion is pivotal with respect to said distal portion and fitting.

36. The multiple port adaptor assembly according to claim 35, wherein the flexible portion of the adaptor body is sufficiently flexible for the at least one of the first proximal channel and the second proximal channels which is out of axial alignment with the distal channel may be manipulated into axial alignment with the proximal channel.

37. The multiple port adaptor assembly according to claim 35, wherein at least a portion of the adaptor body is formed from the group consisting of silicone, a flexible plastic and a popoid.

38. The multiple port adaptor assembly according to claim 35, wherein the second proximal channel is offset at an angle between 15 and 30 degrees relative to the axis of the distal channel and wherein the second proximal channel can be moved into axial alignment with the distal channel by manipulation of the adaptor body.

39. A method of advancing medical instruments through a multiple port adaptor, the method comprising the steps of:
  (a) selecting a multiple port adaptor having a distal portion with a distal channel and a proximal portion with first and second proximal channels, the second proximal channel being out of alignment with the distal channel;
  (b) connecting the distal portion of the adaptor body to an endotracheal tube; and
  (c) manipulating the multiple port adaptor to axially align the second proximal channel with the distal channel.

40. The method according to claim 39, further comprising advancing a medical instrument through the second proximal channel while it is axially aligned with the distal channel.

41. The method according to claim 39, wherein the method comprises selecting a multiple port adaptor wherein the first and second proximal channels are each out of axial alignment with the distal channel.

42. The method according to claim 39, wherein the method comprises retaining the second proximal channel in axial alignment with the distal channel.

43. The method according to claim 39, wherein the method comprises selecting an adaptor having at least one seal disposed in one of the first and second proximal channels.

44. The method according to claim 43, wherein the method further comprises advancing a medical instrument through the seal.

45. The method according to claim 44, wherein the adaptor is disposed in pneumatic communication with a ventilation circuit supplying air to the endotracheal tube under PEEP, and wherein the method further comprises maintaining PEEP while the medical instrument extends through the seal.

* * * * *